United States Patent
Eguchi et al.

(10) Patent No.: US 9,778,827 B2
(45) Date of Patent: Oct. 3, 2017

(54) ULTRASONIC DIAGNOSIS APPARATUS

(71) Applicant: HITACHI ALOKA MEDICAL, LTD., Mitaka-shi, Tokyo (JP)

(72) Inventors: Taro Eguchi, Mitaka (JP); Hidetoshi Arii, Mitaka (JP); Toshimitsu Inose, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 734 days.

(21) Appl. No.: 14/359,493

(22) PCT Filed: Nov. 19, 2012

(86) PCT No.: PCT/JP2012/079969
§ 371 (c)(1),
(2) Date: May 20, 2014

(87) PCT Pub. No.: WO2013/077291
PCT Pub. Date: May 30, 2013

(65) Prior Publication Data
US 2014/0325442 A1 Oct. 30, 2014

(30) Foreign Application Priority Data

Nov. 21, 2011 (JP) .................................. 2011-253876
Sep. 28, 2012 (JP) .................................. 2012-215981

(51) Int. Cl.
*G06F 3/048* (2013.01)
*G06F 3/0484* (2013.01)
(Continued)

(52) U.S. Cl.
CPC .......... *G06F 3/04842* (2013.01); *A61B 8/465* (2013.01); *A61B 8/467* (2013.01); *G06F 3/0482* (2013.01); *G06F 19/321* (2013.01)

(58) Field of Classification Search
CPC ..... G06F 19/321; G06F 3/0482; A61B 8/465; A61B 8/467
See application file for complete search history.

(56) References Cited

U.S. PATENT DOCUMENTS 5,161,535 A * 11/1992 Short ...................... A61B 8/00
345/173
5,315,999 A 5/1994 Kinicki et al.
(Continued)

FOREIGN PATENT DOCUMENTS

CN 1722069 A 1/2006
JP 6-319733 A 11/1994
(Continued)

OTHER PUBLICATIONS

LOGIQ 9 Quick Guide, taken from http://www.soundvet.com/assets/Knobology/L9_Quick_Guide.pdf, published Nov. 1, 2001, 2 pages.*

(Continued)

*Primary Examiner* — William Bashore
*Assistant Examiner* — Gregory A Distefano
(74) *Attorney, Agent, or Firm* — Westerman, Hattori, Daniels & Adrian, LLP

(57) ABSTRACT

In the present invention, a plurality of functions are allocated to respective rotary encoders (RE1 to RE5) from among numerous functions involved in ultrasonic diagnosis, and each of the rotary encoders selectively targets for operation each of the allocated plurality of functions. Names for the plurality of functions allocated to each of the rotary encoders are displayed as a bundle within respectively corresponding function menus (FM1 to FM5). Within each of the function menus, the name of the function that is currently being targeted for operation is given a special display mode. For example, the function menu (FM1) displays BbH and AIP, which are the names for two functions allocated to the rotary (Continued)

encoder (RE1), the lower AIP being displayed at a lower brightness than the higher BbH, to explicitly show that the current target for operation is BbH.

11 Claims, 6 Drawing Sheets

(51) Int. Cl.
*G06F 19/00* (2011.01)
*A61B 8/00* (2006.01)
*G06F 3/0482* (2013.01)

(56) References Cited

U.S. PATENT DOCUMENTS

| | | | | |
|---|---|---|---|---|
| 5,553,620 | A * | 9/1996 | Snider | G01S 7/52036 600/440 |
| 2002/0173721 | A1 * | 11/2002 | Grunwald | A61B 8/00 600/437 |
| 2004/0027793 | A1 * | 2/2004 | Haraguchi | G06F 1/162 361/679.55 |
| 2006/0001772 | A1 | 1/2006 | Hsieh | |
| 2009/0247874 | A1 * | 10/2009 | Kim | A61B 8/00 600/443 |
| 2010/0217128 | A1 * | 8/2010 | Betts | A61B 8/14 600/459 |

FOREIGN PATENT DOCUMENTS

| | | |
|---|---|---|
| JP | 2000-152933 A | 6/2000 |
| JP | 2001-104310 A | 4/2001 |
| JP | 2007-235 A | 1/2007 |
| JP | 2007-159922 A | 6/2007 |
| JP | 2008-29468 A | 2/2008 |

OTHER PUBLICATIONS

Office Action dated Feb. 12, 2013 issued in Corresponding Japanese Patent Application No. 2012-215981, OA previously submitted in IDS on May 20, 2014, now with Revised English Translation (6 pages).
Notification of Transmittal of Translation of the International Preliminary Report on Patentability (Form PCT/IB/338) of International Application No. PCT/JP2012/079969 mailed May 22, 2014 with Form PCT/IPEA/409 (4 pages).
Notice of Grounds for Rejection dated Feb. 12, 2013 issued in corresponding application No. JP2012215981.
International Search Report dated Feb. 19, 2013 issued in corresponding application No. PCT/JP2012/079969.
Office Action dated Jun. 16, 2015, issued in counterpart Chinese patent application No. 201280057242.3, with English translation (16 pages).
Office Action dated Jun. 2, 2016, issued in counterpart Chinese Patent Application No. 201280057242.3, with English translation. (11 pages).
Office Action dated Nov. 29, 2016, issued in counterpart Chinese Application No. 2012800572423, with English translation (10 pages).
Office Action dated Feb. 22, 2016, issued in counterpart Chinese Patent Application No. 201280057242.3, with English translation. (24 pages).

* cited by examiner

| NAME OF FUNCTION SET | NAME OF FUNCTION | CONTENT OF FUNCTION | ROTARY ENCODER |
|---|---|---|---|
| Image Func B1 | BbH | HARMONIC IMAGING SETTING | RE1 |
| | IP Select(B) | COMBINATION PATTERN SETTING | RE2 |
| | Image Freq(B/M) | TRANSMISSION FREQUENCY SETTING | RE3 |
| | Focus(B) | FOCUS SETTING | RE4 |
| | Spatial Compound | SPATIAL COMPOUND SETTING | RE5 |
| | AIP | ADAPTED IMAGE PROCESS SETTING | RE1 |
| | AIP Level | AIP LEVEL SETTING | RE2 |
| | ... | ... | ... |
| Image Func B2 | Contrast(B) | CONTRAST SETTING | RE1 |
| | Frame Rate(B) | FRAME RATE SETTING | RE2 |
| | ... | ... | ... |
| ... | | | |

FIG. 4

ULTRASONIC DIAGNOSIS APPARATUS

TECHNICAL FIELD

The present invention relates to an ultrasound diagnostic apparatus, and in particular to setting of a function related to ultrasound diagnosis.

BACKGROUND ART

Ultrasound diagnostic apparatuses have a plurality of functions related to diagnosis, and users of the ultrasound diagnostic apparatus suitably set the functions according to the contents of the diagnosis or the like, for diagnosis. In recent years, the performances of the ultrasound diagnostic apparatus have been significantly improved, and, accordingly, the number of functions related to the diagnosis is also increasing. Because of this, the ultrasound diagnosis apparatus is desirably designed such that the user can easily set a large number of functions.

Because a typical ultrasound diagnostic apparatus has a display for displaying an ultrasound image, the setting contents or the like of the functions may be displayed on the display, to provide an environment where setting by the user is facilitated. For example, a touch panel may be employed for the display, and operation buttons of the functions and setting contents or the like may be displayed on the touch panel, so that the user can directly set the functions through the touch panel while checking the displayed contents.

However, due to restrictions on the design of the ultrasound diagnostic apparatus or on cost, for example, it may not always be possible to equip the touch panel in the ultrasound diagnostic apparatus.

Patent Document 1 discloses a technique where a desired function is enabled from among a plurality of functions assigned to a manual adjustment device. Patent Document 2 discloses an ultrasound diagnostic apparatus in which functions such as a switch provided in the ultrasound probe or the like can be selected by the user according to the user's preferences. Patent Document 3 also discloses a technique where a plurality of functions are assigned to operation switches.

RELATED ART REFERENCES

Patent Documents

[Patent Document 1] JP 2000-152933 A
[Patent Document 2] JP 2001-104310 A
[Patent Document 3] JP 2008-29468 A

DISCLOSURE OF INVENTION

Technical Problem

In consideration of the background art described above, the present inventors have researched and developed a new technique related to the user operation which does not rely on, for example, the touch panel. In particular, the inventors have considered cooperation between an operation device and the display.

The present invention has been made in view of these circumstances, and an object thereof is to improve the usability of the user by visually cooperating the operation device and the display on the display device.

Solution to Problem

According to one aspect of the present invention, there is provided an ultrasound diagnostic apparatus comprising: a plurality of operation devices that receive from a user an operation for setting a function related to ultrasound diagnosis; and a display that displays a name of a function which is set through the plurality of operation devices, wherein a plurality of functions from among a large number of functions related to the ultrasound diagnosis are assigned to each of the plurality of operation devices, and each of the operation devices selectively sets each of the plurality of functions assigned to the operation device as an operation target, and the display displays, for each of the operation devices, a function menu collectively showing names of the plurality of functions assigned to the operation device, and displays a name of a function which is currently the operation target with a special display form in the function menu.

In the above-described configuration, the plurality of functions assigned to each operation device may be set as a default or by the user. Specific examples of the operation device include a rotary encoder, a slider, a trackball, etc. For each operation device, a function menu collectively showing the names of the plurality of functions assigned to the operation device is displayed. The name of the function is desirably shown with text, for example, but may alternatively be shown with a symbol or the like corresponding to the function. A plurality of function menus corresponding to the plurality of operation devices are displayed on the display. In each function menu, the name of the function which is currently the operation target is shown in a special display form. For example, the name of the function which is the current operation target is displayed with a higher brightness than the other names. Alternatively, the current operation target may be explicitly shown by a display position or a display color, or the current operation target may be explicitly shown by an additional display such as a mark.

According to the above-described configuration, because a function menu is displayed on the display for each operation device, it becomes possible, for example, for the user to visually understand the plurality of functions assigned to each operation device and the function which is the current operation target, based on the function menu displayed on the display.

According to another aspect of the present invention, preferably, the plurality of operation devices are placed on an operation panel in a regular arrangement, and the display displays the plurality of function menus corresponding to the plurality of operation devices according to the regular arrangement. For example, when the plurality of operation devices are arranged in one line in the horizontal direction on the operation panel, the plurality of function menus are also arranged in one line in the horizontal direction on the display. Alternatively, when the plurality of operation devices are arranged in one line along the vertical direction on the operation panel, the plurality of function menus are also arranged in one line in the vertical direction on the display.

According to another aspect of the present invention, preferably, the display displays the plurality of function menus while correlating an order of arrangement of the operation devices and an order of arrangement of the function menus related to the operation devices with each other.

According to another aspect of the present invention, preferably, the ultrasound diagnostic apparatus sets a plurality of functions to be assigned to the plurality of operation devices at once as a function set, stores a plurality of the function sets which differ from each other, and assigns the plurality of functions to the plurality of operation devices according to a function set selected by the user from among the plurality of stored functions sets.

According to another aspect of the present invention, preferably, the ultrasound diagnostic apparatus further comprises: an operation function processor that assigns a plurality of functions to each of the plurality of operation devices; and a function menu processor that displays the function menu on the display, wherein the operation function processor changes an active function which is the current operation target of the operation device according to a function change operation from the user on the operation device, and the function menu processor displays, in the function menu corresponding to each of the operation devices, a name of the active function which is the current operation target at an upper part and a name of a non-active function which is not the current operation target at a lower part.

According to the above-described configuration, the name of the active function which is the current operation target is displayed at an upper part and the name of the non-active function which is not the current operation target is displayed at a lower part. Because of this, a user having an intuitive sense of order of upper and lower parts can intuitively and instantaneously understand the assignment of the active function and the non-active function. With this configuration, visibility and flexibility can be significantly improved for the user.

According to another aspect of the present invention, preferably, the function menu processor displays, in the function menu corresponding to each of the operation devices, an operation state mark indicating an operation state of the active function which is the current operation target at the upper part, and the function menu processor changes a display form of the operation state mark of the active function according to whether the active function is being activated, the active function is not activated but can be activated, or the active function cannot be activated.

According to the above-described configuration, the user can immediately recognize the operation state of the active function based on the difference in the display form of the operation state mark, and thus, flexibility can be further improved.

According to another aspect of the present invention, preferably, the function menu processor displays, in the function menu corresponding to each of the operation devices, setting contents related to the active function which is the current operation target at a middle part.

According to the above-described configuration, because the setting contents related to the active function are displayed on the middle part, the user can instantaneously understand the setting contents, and, in addition, because the setting contents displayed at the middle part separate the display at the upper part and the display at the lower part, the visual identification of the upper and lower parts can be further improved.

According to another aspect of the present invention, preferably, the function menu processor displays, in the function menu corresponding to each of the operation devices, an operation state mark indicating an operation state of a non-active function which is not the current operation target at the lower part, and the function menu processor changes a display form of the operation state mark of the non-active function according to whether the non-active function is being activated, the non-active function is not activated but can be activated, or the non-active function cannot be activated.

According to the above-described configuration, because the user can immediately recognize the operation state of the non-active function based on the difference in the display form of the operation state mark, flexibility can be further improved. In addition, for example, by unifying the rules for changing the display forms of the operation state marks of the active function and the non-active function, it becomes possible to provide a unified sense of identification for the user.

According to another aspect of the present invention, the operation function processor changes the active function which is the current operation target of each of the operation devices every time the user applies a function change operation on the operation device, and the function menu processor displays, in an alternately switching manner and in the function menu corresponding to each of the operation devices, the name of the active function at the upper part and the name of the non-active function at the lower part every time the user applies the function change operation on the operation device.

According to another aspect of the present invention, preferably, each of the operation devices is a rotary encoder, a function which is the current operation target of the rotary encoder is changed by a push operation on the rotary encoder, and a setting of the function which is the current operation target is changed by a rotation operation on the rotary encoder.

Advantageous Effects of Invention

According to various aspects of the present invention, the operation device and the display on the display device can be visually integrated and the usability for the user can be improved. For example, according to a preferred configuration of the present invention, the user can visually understand, based on the function menu displayed on the display, the plurality of functions assigned to each operation device and a function which is the current operation target.

BRIEF DESCRIPTION OF DRAWINGS

FIG. 4 is a diagram showing a specific example of a plurality of function sets.

BEST MODE FOR CARRYING OUT THE INVENTION

Figure 1:
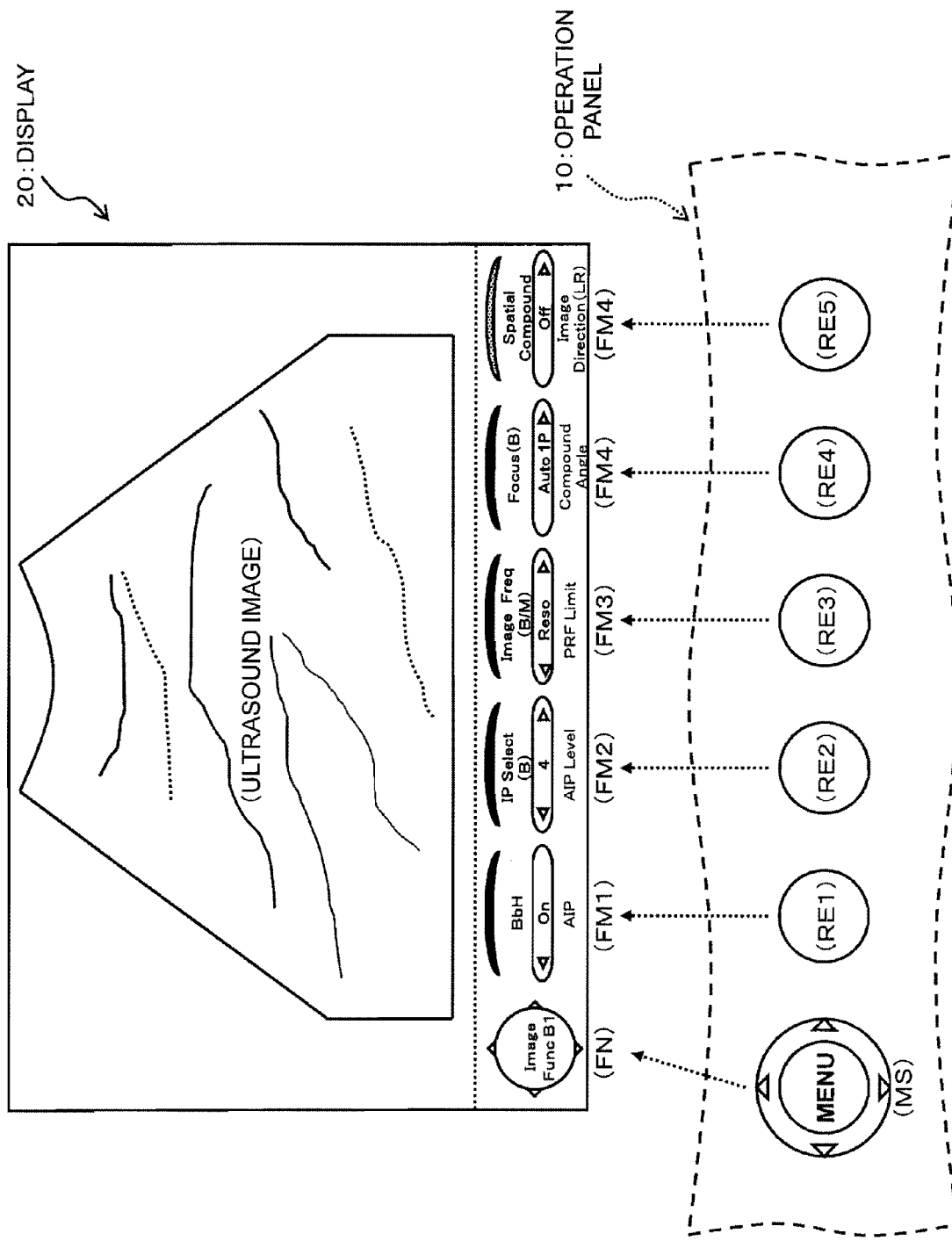
FIG. 1 is a diagram showing an ultrasound diagnostic apparatus preferable in realizing the present invention.

FIG. 1 is a diagram showing an ultrasound diagnostic apparatus preferable in the present invention ("present ultrasound diagnostic apparatus"). FIG. 1 shows a part of an operation panel 10 and a display 20 equipped in the present ultrasound diagnostic apparatus. The operation panel 10 comprises various operation devices which receive operations from a user. For example, various operation devices such as a keyboard, a trackball, a slider, etc., are provided.

FIG. 1 shows a part of the operation panel 10 having various operation devices, and shows 5 rotary encoders (RE1~RE5) and a menu switch (MS).

Each of the rotary encoders (RE1~RE5) has a shape protruding in a circular cylindrical shape, receives a rotation operation from the user by being rotated in a circumferential direction, and receives a push operation from the user by being pushed in the height direction. The menu switch (MS) comprises a select button placed at the center and direction buttons placed around the select button and corresponding to four directions of up, down, left, and right.

The display 20 is a display device which displays various types of information related to diagnosis. As shown in FIG. 1, the display 20 displays ultrasound images such as a B-mode image, an M-mode image, a Doppler measurement image, and a color Doppler image. In addition, in FIG. 1, the display 20 displays 5 function menus (FM1~FM5), and a function set name (FN). The 5 function menus (FM1~FM5) respectively correspond to the rotary encoders (RE1~RE5).

The number of rotary encoders may be a number other than 5. The function menus are provided in a number equal to the number of the rotary encoders.

The ultrasound diagnostic apparatus of FIG. 1 has a large number of functions related to the ultrasound diagnosis. A plurality of functions among the large number of functions are assigned to each of the rotary encoders (RE1~RE5), and each rotary encoder selectively sets each of the plurality of the assigned functions as an operation target. Names of the plurality of functions assigned to each rotary encoder are displayed collectively in the corresponding function menu. In addition, the name of the function which is currently the operation target is displayed with a special display form in the function menu.

For example, in the example configuration of FIG. 1, 2 functions are assigned to the rotary encoder (RE1), and, in the function menu (FM1) corresponding to the rotary encoder (RE1), the names of the 2 functions, "BbH" and "AIP," are displayed. Of the 2 functions, "BbH," which is the current operation target, is placed at an upper part, and the "AIP" at a lower part is displayed with a lower brightness than the "BbH" at the upper part, to explicitly show that the current operation target is "BbH."

Similarly, 2 functions are assigned to each of the other rotary encoders (RE2~RE5), and the names of these functions are collectively displayed in the corresponding function menus (FM2~FM5). In the example configuration of FIG. 1, all of the names of the functions which are the current operation targets are placed at the upper part.

With a push operation on each rotary encoder, the function which is the current operation target of the rotary encoder is changed, and, with a rotation operation on each rotary encoder, the setting contents of the function which is the current operation target are changed.

According to the ultrasound diagnostic apparatus of FIG. 1, because function menus (FM1~FM5) corresponding respectively to the rotary encoders (RE1~RE5) are displayed on the display 20, for example, a user such as the inspector can visually understand, based on the function menus displayed on the display 20, the plurality of functions assigned to the rotary encoders, and the function which is the current operation target. In addition, with the display of the function menus in a manner to be described below, the convenience of the apparatus is further improved.

Figure 2:
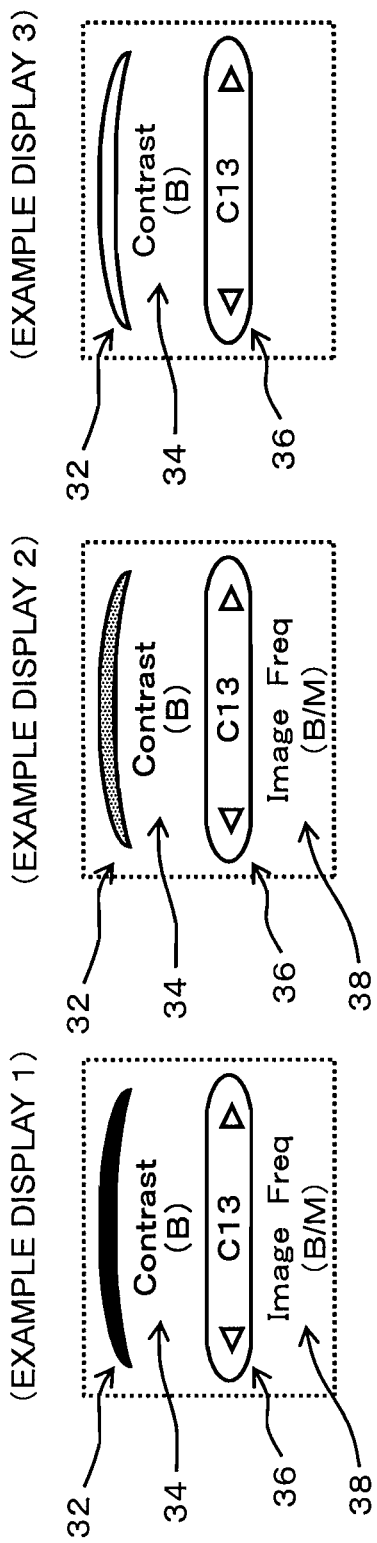
FIG. 2 is a diagram showing an example display of each function menu.

FIG. 2 is a diagram showing an example display of the function menus. FIG. 2 shows example displays 1~3 related to one function menu corresponding to one rotary encoder. In one function menu, an operation state mark 32, an active function 34, a setting content 36, and a non-active function 38 are displayed, in that order from the top.

The active function 34 and the non-active function 38 show names of two functions assigned to the rotary encoder corresponding to the function menu. Of the two functions, the name of the function which is the current operation target is shown in the active function 34, and the name of the function which is not the current operation target is shown in the non-active function 38. In a case where only the active function 34 is assigned and the non-active function 38 is not assigned, for example, the display of the non-active function 38 is omitted, as shown in the example display 3.

The active function 34 is explicitly shown with a special display form. For example, the active function 34 is displayed with a higher brightness than the non-active function 38. Alternatively, the active function 34 may be displayed in color while the non-active function 38 is displayed in black-and-white. Alternatively, the active function 34 may be displayed always above the non-active function 38, to explicitly show the active function 34.

A setting value related to the active function 34 is displayed in the setting content 36. For example, when the function corresponding to the active function 34 is a function which sets a certain numerical value, the numerical value which is currently set is displayed in the setting content 36. In addition, when a value which is larger than the currently set numerical value can be set, a triangular mark is provided to the right of the numerical value, and, when a value which is smaller than the currently set value can be set, a triangular mark is provided to the left of the numerical value. When the function corresponding to the active function 34 is merely a switching operation between an ON state (set state) and an OFF state (non-set state), the state of ON or OFF is displayed in the setting content 36.

The operation state mark 32 indicates an operation state of the active function 34. For example, in the current diagnostic content (currently displayed ultrasound image), a display form of the operation state mark 32 is changed according to whether the function indicated by the active function 34 is being activated, the function is non-activated but can be activated, or the function cannot be activated. For example, the operation state mark 32 of the example display 1 shows that the active function 34 (Contrast (B)) is being activated. Similarly, the operation state mark 32 of example display 2 shows that the active function 34 is not activated, but can be activated. Finally, the operation state mark 32 of the example display 3 shows that the active function 34 cannot be activated.

Alternatively, the operation state of the active function 34 may be indicated with display colors of the operation state mark 32. For example, the operation state mark 32 in the example display 1 may be set to an orange color, the operation state mark 32 in the example display 2 may be set to a blue color, and the operation state mark 32 of the example display 3 may be set to a gray color.

Figure 3:
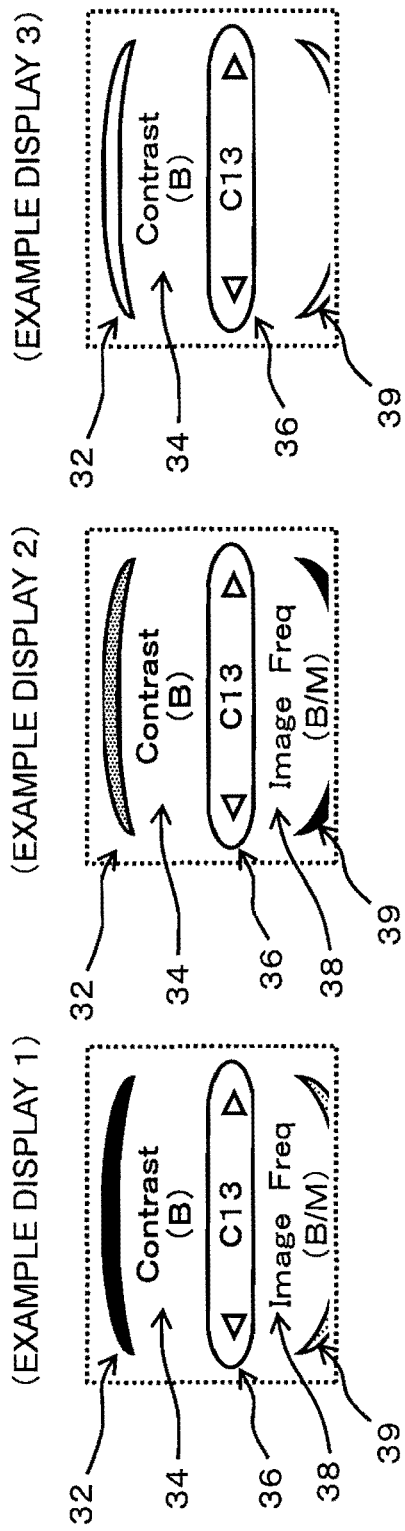
FIG. 3 is a diagram showing another example display of each function menu.

FIG. 3 is a diagram showing another example display of the function menu. FIG. 3 shows example displays 1~3 related to one function menu corresponding to one rotary encoder. A difference from the example displays 1~3 shown in FIG. 2 is that an operation state mark 39 is provided at a lower part of the function menu in FIG. 3.

The operation state mark 39 indicates an operation state of the non-active function 38. For example, in the current diagnosis content (currently displayed ultrasound image), the display form of the operation state mark 39 is changed according to whether the function indicated by the non-active function 38 is being activated, the function is not activated but can be activated, or the function cannot be activated. For example, the operation state mark 39 of the example display 1 shows that the non-active function 38 (Image Freq (B/M)) is not activated but can be activated. Similarly, the operation state mark 39 of the example display 2 shows that the non-active function 38 is being activated. Finally, the operation state mark 39 of the example display 3 shows that no non-active function 38 is assigned, and the non-active function 38 cannot be activated. In the case where no non-active function 38 is assigned, the operation state mark 39 of the non-active function 38 does not need to be displayed. In other words, the display of the operation state mark 39 in the example display 3 may be omitted.

Similar to the case of the operation state mark 32, the operation state of the non-active function 38 may alternatively be shown by display colors of the operation state mark 39. For example, the operation state mark 39 in the example display 1 may be set to a blue color, the operation state mark 39 in the example display 2 may be set to an orange color, and the operation state mark 39 in the example display 3 may be set to a gray color.

The display forms of the operation state mark 32 of the active function 34 at the upper part and the operation state mark 39 of the non-active function 38 at the lower part are preferably changed according to the same rule. For example, when the corresponding function is being activated, both the operation state mark 32 and the operation state mark 39 may be set to the orange color; when the corresponding function is not activated but can be activated, both the operation state mark 32 and the operation state mark 39 may be set to the blue color; and, when the corresponding function cannot be activated, both the operation state mark 32 and the operation state mark 39 may be set to the gray color. Alternatively, the operation state mark 32 of the active function 34 at the upper part may be displayed with a high brightness, and the operation state mark 39 of the non-active function 38 at the lower part may be displayed with a low brightness.

Referring again to FIG. 1, when a plurality of functions which are assigned to the rotary encoders (RE1~RE5) at once are considered as one function set, the one function set is displayed in the function menus (FM1~FM5). In the ultrasound diagnostic apparatus of FIG. 1, a plurality of function sets, in place of one function set, are stored in a memory or the like. A plurality of functions are assigned to the rotary encoders (RE1~RE5) according to one function set selected by the user, for example, and the corresponding function menus (FM1~FM5) are displayed.

FIG. 4 is a diagram showing a specific example of the plurality of function sets. FIG. 4 shows a correspondence between the plurality of function sets and the plurality of functions or the like included in each function set. In the column of name of function set," a name given to each function set is shown. FIG. 4 shows 2 function sets including "Image Func B1" and "Image Func B2." Alternatively, a plurality of function sets in a greater number may be provided.

In the column "name of function," the names of the plurality of functions included in each function set are shown. For example, the function set "Image Func B1" includes a plurality of functions such as "BbH," "IP Select (B)," and "Image Freq (B/M)." In the column "content of function," the content which is set by each function is shown, and, in the column "rotary encoder," a correspondence between each function and the rotary encoder is shown. For example, in "Image Func B1," 2 functions "BbH" and "AIP" are correlated to the rotary encoder RE1, and 2 functions "IP Select (B)" and "AIP Level" are correlated to the rotary encoder RE2. In "Image Func B2," the function "Contrast (B)" is correlated to the rotary encoder RE1 and the function "Frame Rate (B)" is correlated to the rotary encoder RE2.

Here, "Image Func B1" is a function set in which functions which are frequently used for the B-mode image are collected, and is set, for example, as a default in the ultrasound apparatus. In contrast, "Image Func B2" is an optional functional set related to the B-mode image, and is, for example, freely set by the user. In other words, the user can set which function is to be assigned to which rotary encoder according to the user's preferences or the like. Alternatively, the plurality of function sets may be set by the user, or the setting content of the "Image Func B1" which is set as the default may be modified by the user.

In a state where the plurality of function sets are stored in the ultrasound diagnostic apparatus, when, for example, the user selects "Image Func B1," a plurality of functions are assigned to each of the plurality of rotary encoders (RE1~RE5) according to the correspondence shown in "Image Func B1." In addition, when the user selects "Image Func B2," the plurality of functions are assigned to each of the plurality of rotary encoders (RE1~RE5) according to the correspondence shown in "Image Func B2."

For the selection of the function set, for example, the menu switch (MS) shown in FIG. 1 is used. In other words, the user operates the menu switch (MS) to select a desired function set. In addition, the name of the selected function set is displayed in the function set name (FN) in the display 20 shown in FIG. 2, and the content of the function set; that is, the correspondence between the rotary encoder and the plurality of functions, is reflected in the function menus (FM1~FM5).

FIG. 4 shows a plurality of function sets such as "Image Func B1" related to the B-mode image, but alternatively, a plurality of function sets related to other diagnostic content may be further provided. For example, a plurality of function sets related to the M-mode image, a plurality of function sets related to the Doppler measurement image, and a plurality of function sets related to the color Doppler image, etc., may be provided. The contents of these function sets also may be freely set by the user, for example.

Figure 5:
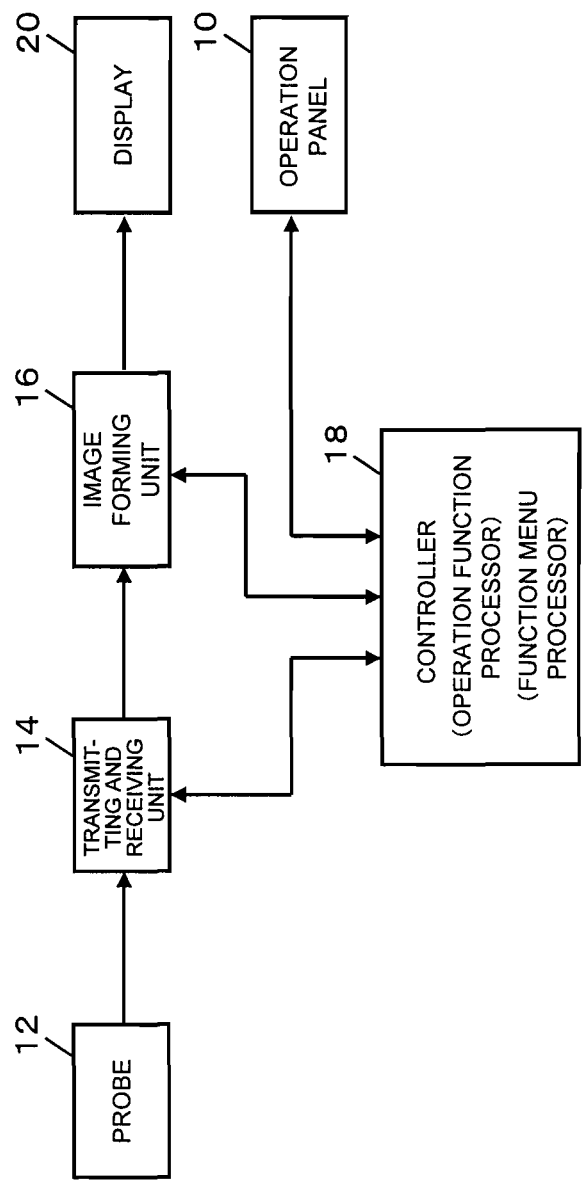
FIG. 5 is a functional block diagram showing an overall structure of the ultrasound diagnostic apparatus.

FIG. 5 is a functional block diagram showing an overall structure of the present ultrasound diagnostic apparatus (FIG. 1). A probe 12 is an ultrasound probe which transmits and receives ultrasound. In the present ultrasound diagnostic apparatus, for example, various probes 12 may be distinguishingly used according to the diagnosis contents, such as, for example, a sector scanning probe, a linear scanning probe, a two-dimensional image (tomographic image) probe, a three-dimensional image probe, or the like.

A transmitting and receiving unit 14 controls transmission of a plurality of transducer elements of the probe 12 to form a transmission beam, and causes a diagnostic area to be scanned by the transmission beam. In addition, the transmitting and receiving unit 14 forms a reception beam by phasing and addition processing of a plurality of reception signals obtained from the plurality of transducer elements, collects the reception signals from the entire area in the diagnostic area, and applies a reception process such as demodulation to the reception signal. With this process, reception data (line data) along each reception beam are obtained. The reception data obtained at the transmitting and receiving unit 14 are sent to an image forming unit 16.

The image forming unit 16 forms an ultrasound image of the diagnostic area based on the reception data collected from the diagnostic area. For example, image data corresponding to the diagnostic content such as the B-mode image (tomographic image), three-dimensional image, Doppler image, or the like are formed in the image forming unit 16. The image forming unit 16 forms a display image including the ultrasound image, and the display image is displayed on the display 20. For example, the display image shown in FIG. 1 is displayed on the display 20.

A controller 18 comprehensively controls the present ultrasound diagnostic apparatus. In the controller 18, a part responsible for control of the operation panel 10 will hereinafter be called an operation function processor, and a part responsible for control of the function menu will hereinafter be called a function menu processor.

The assignment of the functions to the plurality of rotary encoders (RE) of the operation panel 10 and the operation using each rotary encoder are as already explained with reference to FIG. 1. In addition, with regard to the function menu displayed on the display 20 also, processes already described with reference to FIGS. 2 and 3 are applied.

The operation function processor in the controller 18 of FIG. 5 assigns the plurality of functions to each of the plurality of rotary encoders of the operation panel 10, and changes the active function of each rotary encoder according to the function change operation from the user on the rotary encoder; that is, the push operation. The operation function processor changes the active function of each rotary encoder every time the push operation is applied on the rotary encoder.

The operation function processor refers to a table of the plurality of function sets shown in FIG. 4, for example, and assigns the plurality of functions to each of the plurality of rotary encoders (RE), for example, in response to the operation of the user of selecting the "Image Func B1," and according to the correspondence shown in the "Image Func B1." When the user selects the "Image Func B2," the plurality of functions are assigned to each of the plurality of rotary encoders (RE) according to the correspondence shown in the "Image Func B2."

The function menu processor in the controller 18 of FIG. 5 controls the image forming unit 16 which forms the display image of the function menu, to display the function menu on the display 20. The function menu processor displays, in the function menu corresponding to each rotary encoder, the name of the active function which is the current operation target at the upper part, and the name of the non-active function which is not the current operation target at the lower part.

Further, the function menu processor displays, in the function menu corresponding to each rotary encoder, the operation state mark indicating the operation state of the active function at the upper part, the setting content related to the active function at the middle part, and the operation state mark showing the operation state of the non-active function at the lower part.

In addition, every time the push operation is applied to each rotary encoder, the function menu processor also displays in an alternately switching manner in the function menu corresponding to that rotary encoder the name of the active function at the upper part and the name of the non-active function at the lower part.

In this manner, the assignment of the functions to the plurality of rotary encoders (RE) and operation using each rotary encoder described above with reference to FIG. 1 are realized, and the example displays of the function menus displayed on the display 20 described above with reference to FIGS. 2 and 3 are realized.

Figure 6:
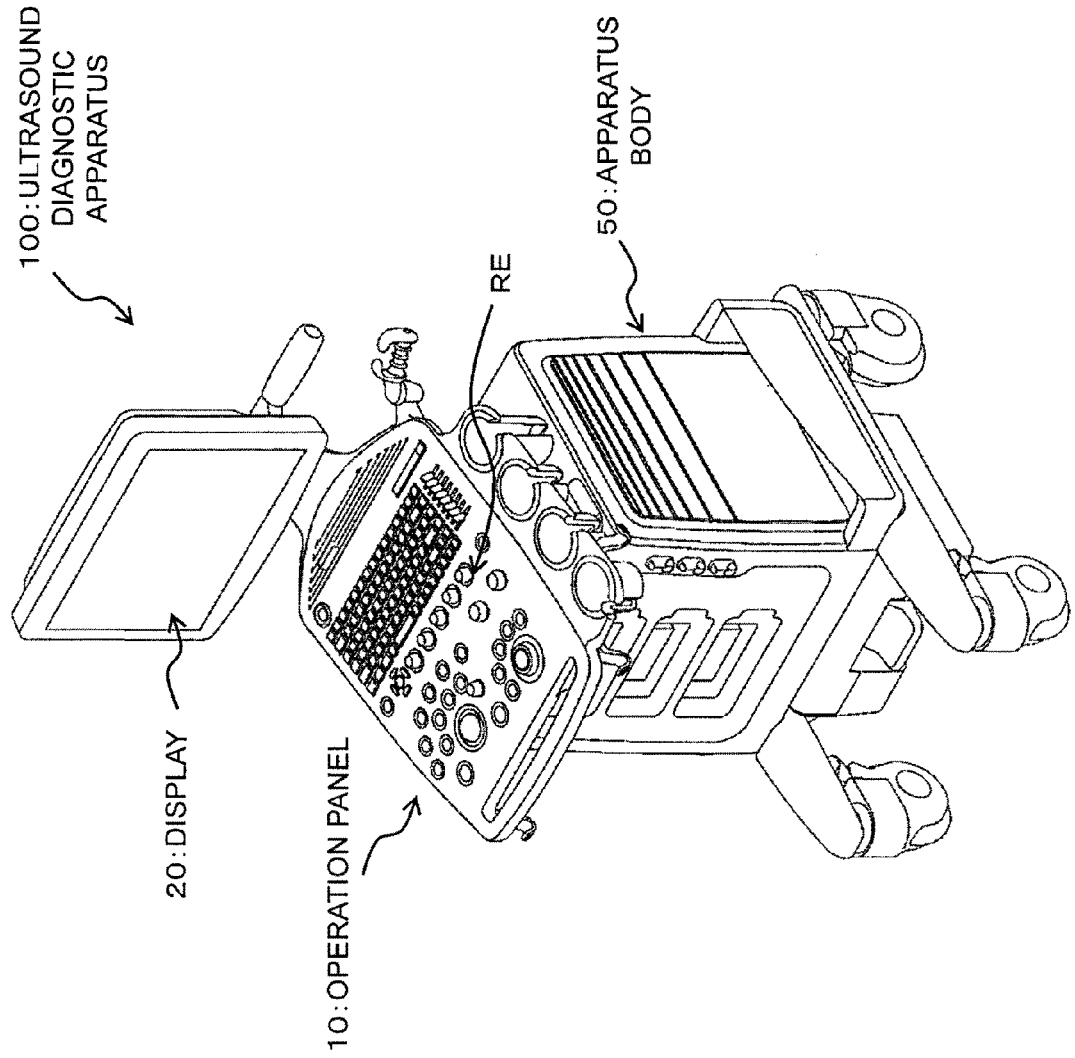
FIG. 6 is a perspective diagram showing an overall outer appearance of the ultrasound diagnostic apparatus.

FIG. 6 is a perspective diagram showing an overall outer appearance of the present ultrasound diagnostic apparatus 100. The present ultrasound diagnostic apparatus 100 has an apparatus body 50 which is supported by a base portion having 4 casters, an operation panel 10 supported by pillars protruding from the apparatus body 50 and placed above the apparatus body 50, and the display 20 held by an arm mechanism provided on the operation panel 10. On an operation surface of the operation panel 10, the rotary encoder (RE), keyboard, trackball, and the like is placed.

In the overall structure of the present ultrasound diagnostic apparatus 100, the operation panel 10 and the display 20 are placed in a close-distance relationship. The operation panel 10 is slightly tilted with respect to the horizontal plane such that the operation surface is oriented toward the user side (front side in FIG. 6). The display 20 is used with its display surface approximately vertical. As described above with reference to FIG. 1, 5 function menus are displayed on the display surface of the display 20, and each of the 5 function menus is correlated to one of the rotary encoders (RE) of the operation panel 10.

A preferred embodiment of the present invention has been described. The above-described embodiment is merely exemplary in every aspect, and is not to be interpreted as limiting the scope of the present invention. The present invention includes various modified forms within the scope and spirit of the invention.

EXPLANATION OF REFERENCE NUMERALS

10 OPERATION PANEL; 20 DISPLAY; 32 OPERATION STATE MARK; 34 ACTIVE FUNCTION; 36 SETTING CONTENT; 38 NON-ACTIVE FUNCTION.

The invention claimed is:

1. An ultrasound diagnostic apparatus comprising:
a plurality of operation devices that receive an operation for setting a function related to ultrasound diagnosis from a user;
a display that displays a name of a function which is set through the plurality of operation devices,
wherein a plurality of functions from among a large number of functions related to the ultrasound diagnosis are assigned to each of the plurality of operation devices, and each of the operation devices selectively sets each of the plurality of functions assigned to the operation device as an operation target, and
wherein the display displays, for each of the operation devices, a function menu showing names of the plurality of functions assigned to the operation device, and displays, in the function menu, a name of an active function which is currently the operation target, a name of a non-active function which is not currently the operation target, and setting contents related to the active function between the name of the active function and the name of the non-active function;
an operation function processor that assigns the plurality of functions to each of the plurality of operation devices; and
a function menu processor that displays the function menu on the display,
wherein the operation function processor changes an active function which is the current operation target of the operation device according to a function change operation from the user on the operation device,
wherein the function menu processor displays, in the function menu corresponding to each of the operation devices, a name of the active function which is the current operation target at an upper part and a name of a non-active function which is not the current operation target at a lower part, wherein the operation function processor changes the active function which is the current operation target of each of the operation devices every time the user applies the function change operation on the operation device, and wherein the function menu processor displays, in an alternately switching manner and in the function menu corresponding to each of the operation devices, the name of the active function at the upper part and the name of the non-active function at the lower part every time the user applies the function change operation on the operation device.

2. The ultrasound diagnostic apparatus according to claim 1, wherein the plurality of operation devices are placed on an operation panel in a regular arrangement, and the display displays the plurality of function menus corresponding to the plurality of operation devices according to the regular arrangement.

3. The ultrasound diagnostic apparatus according to claim 2, wherein the display displays the plurality of function menus while correlating an order of arrangement of the operation devices and an order of arrangement of the function menus related to the operation devices with each other.

4. The ultrasound diagnostic apparatus according to claim 3, wherein the plurality of functions to be assigned to the plurality of operation devices at once are set as a function set, a plurality of the function sets which differ from each other are stored, and the plurality of functions are assigned to the plurality of operation devices according to a function set selected by a user from among the plurality of stored function sets.

5. The ultrasound diagnostic apparatus according to claim 1, wherein the function menu processor displays, in the function menu corresponding to each of the operation devices, an operation state mark indicating an operation state of the active function which is the current operation target at the upper part, and the function menu processor changes a display form of the operation state mark of the active function according to whether the active function is being activated, the active function is not activated but can be activated, or the active function cannot be activated.

6. The ultrasound diagnostic apparatus according to claim 1, wherein the function menu processor displays, in the function menu corresponding to each of the operation devices, setting contents related to the active function which is the current operation target at a middle part.

7. The ultrasound diagnostic apparatus according to claim 1, wherein the function menu processor displays, in the function menu corresponding to each of the operation devices, an operation state mark indicating an operation state of a non-active function which is not the current operation target at the lower part, and the function menu processor changes a display form of the operation state mark of the non-active function according to whether the non-active function is being activated, the non-active function is not activated but can be activated, or the non-active function cannot be activated.

8. The ultrasound diagnostic apparatus according to claim 5, wherein the function menu processor displays, in the function menu corresponding to each of the operation devices, an operation state mark indicating an operation state of a non-active function which is not the current operation target at the lower part, and the function menu processor changes a display form of the operation state mark of the non-active function according to whether the non-active function is being activated, the non-active function is not activated but can be activated, or the non-active function cannot be activated.

9. The ultrasound diagnostic apparatus according to claim 1, wherein each of the operation devices is a rotary encoder, a function which is the current operation target of the rotary encoder is changed by a push operation on the rotary encoder, and a setting of the function which is the current operation target is changed by a rotation operation on the rotary encoder.

10. An ultrasound diagnostic apparatus comprising:

a plurality of operation devices that receive an operation for setting a function related to ultrasound diagnosis from a user;

a display that displays a name of a function which is set through the plurality of operation devices, wherein a plurality of functions from among a large number of functions related to the ultrasound diagnosis are assigned to each of the plurality of operation devices, and each of the operation devices selectively sets each of the plurality of functions assigned to the operation device as an operation target, and wherein the display displays, for each of the operation devices, a function menu showing names of the plurality of functions assigned to the operation device, and displays, in the function menu, a name of an active function which is currently the operation target, a name of a non-active function which is not currently the operation target, and an operation state mark indicating an operation state of the active function at a region nearer to the name of the active function than to the name of the non-active function;

an operation function processor that assigns the plurality of functions to each of the plurality of operation devices; and a function menu processor that displays the function menu on the display, wherein the operation function processor changes an active function which is the current operation target of the operation device according to a function change operation from the user on the operation device, wherein the function menu processor displays, in the function menu corresponding to each of the operation devices, a name of the active function which is the current operation target at an upper part and a name of a non-active function which is not the current operation target at a lower part, wherein the operation function processor changes the active function which is the current operation target of each of the operation devices every time the user applies the function change operation on the operation device, and wherein the function menu processor displays, in an alternately switching manner and in the function menu corresponding to each of the operation devices, the name of the active function at the upper part and the name of the non-active function at the lower part every time the user applies the function change operation on the operation device.

11. An ultrasound diagnostic apparatus comprising:

a plurality of operation devices that receive an operation for setting a function related to ultrasound diagnosis from a user;

a display that displays a name of a function which is set through the plurality of operation devices;

an operation function processor that assigns a plurality of functions from among a large number of functions related to the ultrasound diagnosis to each of the plurality of operation devices; and a function menu processor that displays the function menu on the display, wherein each of the operation devices selectively sets each of the plurality of functions assigned to the operation device as an operation target, the display displays, for each of the operation devices, a function menu collectively showing names of the plurality of functions assigned to the operation device, and displays a name of a function which is currently the operation target with a special display form in the function menu, the operation function processor changes an active function which is the current operation target of the operation device according to a function change operation from the user on the operation device, the function menu processor displays, in the function menu corresponding to each of the operation devices, a name of the active function which is the current operation target at an upper part and a name of a non-active function which is not the current operation target at a lower part, the operation function processor changes the active function which is the current operation target of each of the operation devices every time the user applies the function change operation on the operation device, and the function menu processor displays, in an alternately switching manner and in the function menu corresponding to each of the operation devices, the name of the active function at the upper part and the name of the non-active function at the lower part every time the user applies the function change operation on the operation device.

* * * * *